(12) United States Patent
Yamauchi et al.

(10) Patent No.: US 7,220,873 B2
(45) Date of Patent: May 22, 2007

(54) CONJUGATED FATTY ACID CONTAINING MONOGLYCERIDES AND PROCESS FOR PRODUCING THEM

(75) Inventors: Yoshie Yamauchi, Nagoya (JP); Takaya Yamamoto, Nagoya (JP); Kentaro Tsutsumi, Tokyo-to (JP); Yuji Shimada, Osaka (JP); Yomi Watanabe, Neyagawa (JP); Akio Sugihara, Itami (JP); Yoshio Tominaga, Osaka (JP)

(73) Assignees: The Nisshin Oillio Group, Ltd., Tokyo (JP); Osaka Municipal Government, Osaka (JP)

( * ) Notice: Subject to any disclaimer, the term of this patent is extended or adjusted under 35 U.S.C. 154(b) by 855 days.

(21) Appl. No.: 10/210,207

(22) Filed: Aug. 2, 2002

(65) Prior Publication Data

US 2003/0130533 A1    Jul. 10, 2003

(30) Foreign Application Priority Data

Aug. 2, 2001  (JP)  ............................. 2001-235348
Apr. 24, 2002  (JP)  ............................. 2002-122639

(51) Int. Cl.
    *C11C 3/00*    (2006.01)
(52) U.S. Cl. .................................... 554/167
(58) Field of Classification Search ................. 554/167
    See application file for complete search history.

(56) References Cited

U.S. PATENT DOCUMENTS 6,608,222 B2 *  8/2003  Bonsignore et al. ........ 554/126

FOREIGN PATENT DOCUMENTS

| EP | 0 191 217 A1 | 8/1986 |
|---|---|---|
| EP | 191217 | * 8/1986 |
| FR | 2 648 147 A1 | 12/1990 |
| JP | 61-181390 | 8/1986 |
| WO | WO 97/18320 | 5/1997 |
| WO | 00/18944 | * 4/2000 |
| WO | WO 00/18944 A1 | 4/2000 |
| WO | WO 02/24935 A1 | 3/2002 |
| WO | WO 02/41706 A2 | 5/2002 |

OTHER PUBLICATIONS

Park et al., "Conjugated Linoleic acid (CLA) Glycerol," J. Korean Soc. Food Sci. Nutr., vol. 29, No. 3, 2000, pp. 389-394.
Tomonori, "Production of Fatty Acid Ester of Glycerol," Patent Abstracts of Japan, vol. 1998, No. 02, Jan. 30, 1998, JP 09-268299. Oct. 14, 1997, Abstract.
Arcos, Jose A. et al., "Continous Enzymatic Esterification of Glycerol with (Poly)Unsaturated Fatty Acids in a Packed-Bed Reactor", Biotechnology and Engineering, vol. 68, No. 5, Jun. 5, 2000, pp. 563-570.

* cited by examiner

*Primary Examiner*—Deborah D. Carr
(74) *Attorney, Agent, or Firm*—Foley and Lardner LLP

(57) ABSTRACT

This invention provides monoglycerides containing a conjugated fatty acid, and a process for producing the above described conjugated fatty acid containing monoglycerides in which all kinds of lipases can be used as catalysts.

This invention relate to monoglycerides containing a conjugated fatty acid (preferably in an amount of 50% or more of fatty acids).

This invention also relates to a process for producing the conjugated fatty acid containing monoglycerides, in which the conjugated fatty acid containing a free fatty acid and glycerol are subjected to the reaction of esterification, or of esterification and glycerolysis in the presence of lipase as a catalyst.

16 Claims, No Drawings

CONJUGATED FATTY ACID CONTAINING MONOGLYCERIDES AND PROCESS FOR PRODUCING THEM

BACKGROUND OF THE INVENTION

1. Field of the Invention

This invention relates to conjugated fatty acid containing monoglycerides and a process for preparing them. More particularly, this invention relates to conjugated fatted acid containing monoglycerides which are useful for such purposes as an emulsifier of foods and an additive for beverages, and to a process for preparing the conjugated fatted acid containing monoglycerides by the esterification reaction of conjugated fatty acid containing free fatty acid and glycerol as the substrates in the presence of lipase or by the continuous reaction of esterification and glycerolysis in the same reaction system.

2. Background Art

Conjugated linoleic acid has a variety of physiological activities such as anticarcinogenic, body fat reducing, anti-arteriosclerotic and antiallergic effects, and used as a healthy food in the form of a free fatty acid but not in the form of a monoglyceride. Conventional fatty acid glycerol esters of non-conjugated fatty acids have been used as emulsifiers in various fields of foods, pharmaceuticals and cosmetics, and among them monoglycerides are most conveniently used. Conventional monoglycerides of non-conjugated fatty acids are industrially produced by chemical alcoholysis of oils and fats with two molar equivalents of glycerol in the presence or in the absence of metal catalysts at high temperatures and high pressures.

However, the conventional chemical methods cannot be applied to the preparation of conjugated fatty acid containing monoglycerides which contain unstable conjugated linoleic acid, and in this context no reports concerning conjugated fatty acid containing monoglycerides and the method of preparing them have been made as long as the present inventors are aware.

In addition, the methods for synthesizing monoglycerides of non-conjugated long chain fatty acids utilizing an enzyme reaction are disclosed for example in Japanese Patent Laid-Open Publication No. 268299/1997 and Japanese Patent Publication No. 12112/1992. The former publication proposes the method for synthesizing efficiently a monoglyceride by glycerolysis of a triglyceride in the presence of a lipase derived from genus *Pseudomonas*. However, when a conjugated fatty acid monoglyceride is intended to be prepared by the method, the monoglyceride can be prepared only after the conjugated fatty acid, which is usually available in the form of a free fatty acid, is first converted into a triglyceride. In addition, the latter publication proposes the method for preparing a monoglyceride by esterifying a free fatty acid and a glyceride in the presence of mono- and di-glyceride lipase. In this method, the reaction is carried out at 30° C., so that the monoglyceride content in the total glycerides reaches 90% or more when the esterification degree is 60% or less, while a diglyceride as a by-product is observed and the contents of the monoglyceride and the diglyceride become substantially equivalent when the esterification degree is increased to a level of 90% or more.

Conjugated fatty acids possess a variety of physiological activities and employed as healthy foods in the free fatty acids as described above. The conjugated fatty acids are expected to be supplied in the form of monoglycerides for developing the uses as the additives or emulsifiers to a variety of foods, particularly drinks. However, because of the thermal-unstableness of the conjugated fatty acids as described above, the chemical method which has been conventionally used for the preparation of non-conjugated fatty acid glycerides cannot be applied to the preparation of the conjugated fatty acid glycerides, and the enzymatic methods which have hitherto been proposed for the preparation of non-conjugated fatty acid glycerides can be applied effectively only to the glycerolysis which uses a lipase derived from a specific microorganism (genus *Pseudomonas*) as a catalyst (Japanese Patent Laid-Open Publication No. 268299/1997; J. Am. Oil Chem. Soc., 68, 6–10, 1991) and to the esterification reaction in which the esterification degree is maintained at a low level (Japanese Patent Publication No. 12112/1992).

SUMMARY OF THE INVENTION

The object of this invention is to provide a technique for preparing monoglyceride containing conjugated fatty acids, specifically a technique for preparing a conjugated fatty acid glycerol ester in which all of the lipases including monoglyceride lipase, mono- and di-glyceride lipase, and triglyceride lipase can be employed as catalysts, and conjugated fatty acid glycerol ester having a higher monoglyceride content can be prepared even if the esterification degree is increased.

In consideration of such technical backgrounds, the present inventors have conducted earnest examinations for the purpose of accomplishing the above described object. As a result, they have succeeded in the construction of a reaction system in which esterification is carried out in the presence of a lipase as a catalyst and a reaction system in which a continuous reaction of esterification and glycerolysis is carried out in one reaction system, thus accomplishing the invention on the basis of these findings.

That is, the gists of this invention are the following monoglyceride, a process for preparing and purifying it:

a monoglyceride containing a conjugated fatty acid, preferably the aforementioned monoglyceride containing a conjugated fatty acid (typically conjugated linoleic acid) in an amount of 50% or more in the total fatty acids;

a process for producing the above described conjugated fatty acid containing monoglyceride, characterized in that free fatty acid containing a conjugated fatty acid and glycerol are subjected to the esterification reaction or the esterification and glycerolysis reaction using lipase as a catalyst; and a process for producing the above described monoglyceride, characterized in that in the reaction utilizing esterification, glycerol is employed in an amount of 1–20 moles per mole of the free fatty acid containing the conjugated fatty acid to carry out the reaction at a temperature of 0° C.–20° C. or 20° C.–70° C. to dehydrate under reduced pressure in the middle of the reaction if the temperature is set at 0° C.–20° C. or from the start of the reaction if the temperature is set up at 20° C.–70° C., and to maintain the temperature at 0° C.–20° C. or 20° C.–70° C. until the esterification degree reaches a level of 90% or more (the first method).

The process for producing the above described monoglyceride, characterized in that in the reaction utilizing esterification and glycerolysis, glycerol is employed in an amount of 1–20 moles per mole of the free fatty acid containing the conjugated fatty acid to carry out the esterification reaction at a temperature of 20° C.–70° C., to dehydrate under reduced pressure in the middle of the reaction for enhancing the esterification rate to a level of 90% or more and then cooling (preferably rapidly cooling) the reaction system, and to allow to stand the system at a temperature of 0° C.–20° C. for advancing the glycerolysis reaction (the second method).

A process for deacidification and purification a glyceride product containing or comprising as a major ingredient a monoglyceride, characterized in that alkali is added to the glyceride product comprising or comprising as the major ingredient the monoglyceride in which a free fatty acid is concomitantly present, whereby the free fatty acid present in the product is neutralized to give a saponification product, and a material having a molecular weight larger than the monoglyceride and a compatibility with the saponification product is added for decreasing the concentration of the saponification product, which is then subjected to the molecular distillation to remove the saponification product as a distillation residue.

DETAILED DESCRIPTION OF THE INVENTION

The monoglycerides according to this invention are the monoglycerides containing a conjugated fatty acid as described above, and preferably monoglycerides containing the conjugated fatty acid in an amount of 50% or more (in the total fatty acids esterified with glycerol). Furthermore, the monoglyceride according to this invention is a conjugated fatty acid monoglyceride which contains substantially no triglycerides (2% or less), little free fatty acids (5% or less), and a high amount, usually 50% or more, preferably 70% or more, more preferably 80% or more, particularly 90% or more of monoglyceride within total (mono-, di- and tri-)glycerides.

In this invention, the conjugated fatty acids preferably include for example conjugated linoleic acid, conjugated trienic acid (particularly conjugated linolenic acid), conjugated EPA, conjugated DHA, among which the conjugated linoleic acid is typical.

In this connection, the expression "%" means herein % by weight unless otherwise stated or except the case where the expression % alone will define the meaning (e.g. esterification degree).

Such conjugated fatty acid containing monoglycerides can be prepared, as described above, by subjecting a fatty acid mixture containing the conjugated fatty acid and glycerol to esterification or esterification and glycerolysis reactions in the presence of lipase as a catalyst. The typical embodiments of the method according to this invention include the first method in which the esterification reaction is employed as described above, and the second method in which the esterification and glycerolysis reactions are performed continuously in the same reaction system.

The free fatty acid containing the conjugated fatty acid used in the method of this invention may include those from any sources which contain a conjugated fatty acid as described above, preferably those containing 50% or more, more preferably 70% or more of the conjugated fatty acid. Practical examples of the free fatty acid include preferably a mixture of free fatty acids which contain, respectively, 30% or more of c9,t11- and t10,c12-conjugated linoleic acid isomers prepared by alkaline conjugating an oil containing linoleic acid (e.g. safflower oil and sunflower oil) in the presence of propylene glycol or the like (for example, CLA-80:Rinoru Oil Mills. Co.). The free fatty acids may also be a mixture of fatty acids obtained from a conjugated linoleic acid containing fats and oils produced for example by microorganisms such as lactic bacteria (see e.g. U.S. Pat. No. 6,060,304 in which lactobacillus is used). Furthermore, monoglycerides of interest having a high conjugated linoleic acid content can be finally obtained when free fatty acids having a high conjugated linoleic acid content (e.g., 90% or more) obtained by purification to the desired levels with the means such as the urea adduct fractionation method, the low temperature crystallization method, the methods which use selective reactions with an enzyme (lipase) are used (see, e.g., Lipids, 34, 979–987 (1999), J. Am. Oil Chem. Soc., 76, 1265–1268 (1999), J. Am. Oil Chem. Soc., 79, 303–308 (2002)). The content of the conjugated linoleic acid can be adjusted to a desired ratio by appropriately controlling the purification level in the methods described above, and can be lowered desirably by dilution with non-conjugated fatty acids.

The lipase used as a catalyst may be any one of unpurified, partially purified, or purified enzymes which recognize glycerides as a substrate, and includes monoglyceride lipase, mono- and di-glyceride lipase, as well as triglyceride lipase. Particularly, preferred are the enzymes produced by microorganisms such as genera *Pseudomonas, Burkholderia, Alcaligenes, Bacillus, Candida, Geotrichum, Penicillium, Rhizopus, Rhizomucor, Mucor, Aspergillus*, and *Thermomyces*, and an enzyme derived from porcine pancreas. In general, these enzymes are commercially available and can be obtained easily.

The amount of the lipase as the enzyme used, which is determined by the reaction conditions such as reaction time and reaction temperature, is not specifically defined, but it can be appropriately set up and may be added in an amount of usually 1 U–10,000 U, preferably 5 U–1,000 U per g of a reaction mixture. The phrase 1 U of the lipase (triglyceride lipase) herein means the amount of the enzyme which liberates 1 μmole of a fatty acid per minute in the hydrolysis reaction of olive oil, and the phrase 1 U of monoglyceride lipase or mono- and di-glyceride lipase means the amount of the enzyme which liberates 1 μmole of a fatty acid per minute in the hydrolysis reaction of monoolein. The enzyme may be used in the form of a free type or in the form immobilized on carriers such as ion-exchange resins, porous resins, ceramics, and calcium carbonate. When the free type enzyme is used, it is preferred that the enzyme is first dissolved in water and the enzymatic aqueous solution is added to a reaction mixture so that the enzyme is added in a predetermined amount. In this connection, the enzyme agent is preferably dissolved in water as little as possible. In addition, when the supported enzyme is used, it is not necessary to add water to the reaction system.

The amount of glycerol added to the reaction system is one of the important factors, and particularly influences the esterification degree and the monoglyceride content of the glyceride fraction. The amount of glycerol is usually 1–20 moles, and preferably 2–10 moles per mole of a free fatty acid. When the reaction temperature is set up at 20° C.–70° C. (the second method), the esterification degree can be increased by increasing the amount of glycerol to 7 moles or more per mole of the free fatty acid, even if a small amount of water derived from the enzyme solution present in the reaction system and water generated by the esterification reaction are not specially removed by procedures such as reduced pressure or the like. In addition, while the synthesis of mono-, di- and triglycerides in the reaction at 20° C.–70° C. is scarcely affected by the amount of glycerol, on the reaction at a low temperature of 0° C.–20° C. (the first method) the production of di- and triglycerides as the by-products can be further suppressed by increasing the amount of glycerol to 7 moles or more per mole the free fatty acid in addition to the effect of the reaction at low temperature, thus enhancing the yield ratio of a monoglyceride to total glyceride.

Water derived from the enzyme solution present in the reaction system and water generated by the esterification reaction will greatly affect the esterification reaction in which the amount of glycerol is held down (in the order of from equimolar to 3 or 5 molar amounts). In the reaction of this case (including the first and second methods), it is possible to shorten the time until the esterification reaches 90% or more by dehydration under reduced pressure (usually under vacuum of 0.5–5 mmHg absolute pressure after vacuum) with a vacuum device such as a vacuum pump in the course of the reaction for example at the time when the esterification degree reaches 50–70% or at the start of the reaction if the temperature is set at 20° C.–70° C. in the first method which utilizes the esterification reaction, and to obtain a higher esterification degree as well.

In this connection, the esterification degree herein means the percentage of fatty acids in the produced ester (glyceride) to the total fatty acids in the reaction system.

In the preferred embodiment of the first method utilizing the esterification reaction, one of the preferred methods, at a temperature in the range of 0° C.–20° C., after the start of the reaction using the mixture of a substrate and an enzyme emulsified by the stirring-like operation is a method in which the stirring-like operation is stopped when the fluidity of the mixture is decreased along with the progress of the reaction and finally solidified, and the system is maintained at the above described temperature until the esterification rate reaches 90% or more, preferably 95% or more. Another preferred method at a temperature in the range of 20° C.–70° C. is a method in which the esterification reaction is carried out so that the emulsion is maintained by the stirring-like operation, and the system is maintained at the above described temperature until the esterification degree reaches 90% or more, preferably 95% or more while the stirring operation is continued.

The preferred embodiment of the second method utilizing the esterification reaction and the glycerolysis reaction is a method in which the esterification reaction is carried out with the mixture of a substrate and an enzyme emulsified by the stirring-like operation, and the system is rapidly cooled under the vigorous stirring-like operation until the reaction mixture is solidified after the esterification degree reaches 90% or more, preferably 95% or more.

The esterification reaction until the reaction mixture is solidified is preferably carried out with glycerol having a size of the fluid particles smaller as possible and in a uniform emulsion state. The reaction time may be shortened if the size of the fluid particles of glycerol is decreased. A variety of means for affording the stirring-like operation may be applied to the method for producing an emulsion including various stirrings (for example, stirring styles with a variety of shapes of stirring impeller, stirrers, homogenizers, and mixers), vibration (e.g. sonication-treatment), piston systems, honeycomb systems. If the size of the fluid particles is more decreased, the contact area between glycerol and the fatty acids is further increased, so that esterification reaction can be carried out more efficiently. Such adjustments can be done by appropriately controlling, e.g., the output of the above described means.

In this invention, the reaction temperature is especially important. When the monoglycerides are prepared by the esterification reaction alone (the first method), the production of di- and triglycerides as the by-products can be suppressed by setting up the reaction temperature at 0° C.–20° C., preferably 0° C.–15° C. Furthermore, when the reaction temperature is set at 20° C.–70° C., preferably 25° C.–50° C., the production of di- and triglycerides as the by-products can be suppressed by initiating the dehydration under reduced pressure from the start of the reaction.

When the monoglycerides are prepared by continuously advancing the esterification and glycerolysis reactions in the same reaction system (the second method), the mono- and diglycerides are produced first by conducting the esterification reaction at 20° C.–70° C., preferably 25° C.–50° C. The glycerolysis reaction progresses efficiently at 0° C.–20° C., preferably 0° C.–15° C., resulting in the increased ratio of the monoglyceride in the glyceride fraction. However, in order to progress the glycerolysis reaction after esterification, it is preferred to solidify the reaction mixture by cooling it to the predetermined temperature for the glycerolysis reaction with strong stirring-like operation as described above. In this case, it is preferred to solidify rapidly the mixture by cooling it as rapid as possible, but relatively slow temperature descending rate will not affect significantly the reaction except that solidification requires a longer time. These settings and adjustments of temperature can be performed with conventional thermostats or the like.

The period required for the reaction is not particularly specified, since it is greatly affected by the reaction conditions such as temperature, the amount of an enzyme, and the amount of glycerol. The reaction rate increases along with temperature, and amounts of the enzyme and glycerol. In consideration of the operability, the reaction time in the method utilizing the esterification reaction alone (the first method) is preferably for 10 hours–1 week, more preferably for about 20–96 hours inclusive the reaction time after terminating the stirring operation at a reaction temperature of 0° C.–20° C., while it is preferably for 1–96 hours, more preferably for about 10–72 hours if the reaction is conducted with dehydration under reduced pressure at a reaction temperature of 20° C.–70° C. Furthermore, the reaction time required for esterification, at a reaction temperature of 20° C.–70° C., in the method in which the esterification and glycerolysis reactions are continuously conducted in the same reaction system (the second method) is preferably for 1–72 hours, more preferably about 5–72 hours, and in the subsequent glycerolysis reaction in which diglycerides are converted to monoglycerides at a reaction temperature of 0° C.–20° C., it is preferred to allow to stand the reaction mixture rapidly cooled and solidified usually for 5 hours–2 months, preferably for 1–30 days, more preferably for about 1–10 days. The standing time greatly depends on the means of the above described stirring-like operation for rapid cooling and solidification, and thus the reaction time can be largely shortened by preparing an emulsion having small liquid-particle sizes of glycerol by strong stirring with stirring apparatuses such as a homogenizer or a handy mixer for food processing, and maintaining this state by solidification.

In this connection, if the reaction mixture is frothed up before solidification in the esterification reaction, the conjugated fatty acids tend to be oxidized or isomerized, and thus the reaction mixture is preferably solidified under non-frothed conditions or under the nitrogen stream.

As described above, in the first method utilizing the esterification reaction of lipase, the stirring-like operation, the adjustment of the glycerol concentration, and appropriate dehydration under reduced pressure in the course of the reaction as above or dehydration under reduced pressure from the start of the reaction increase the esterification degree to give the esterification degree of 90% or more, preferably 95% or more within a short time. If the reaction mixture after solidification is allowed to stand at a low temperature, the monoglyceride content of the glyceride fraction in the reaction mixture finally reaches 80% or more. In addition, in the second method in which the esterification reaction of lipase and the glycerolysis reaction are continuously conducted in the same reaction system, appropriate dehydration under reduced pressure particularly in the course of the reaction results in the esterification degree up to 90% or more, preferably 95% or more, and the reaction mixture in this state is completely solidified by the vigorous stirring-like operation and preferably rapid cooling and left standing at a low temperature for further conducting the glycerolysis reaction, thus resulting in the monoglyceride content of the glyceride fraction in the reaction mixture of 80% or more.

It is possible to prepare products comprising the conjugated fatty acid containing monoglycerides of this invention as the main ingredient by the aforementioned method.

In order to refine the monoglyceride from the reaction mixture (products comprising the conjugated fatty acid containing monoglycerides as the main ingredient), if desired, after reaction, it is possible to employ any reasonable methods, among which usual deacidification, deacidification in solvents, membrane separation, distillation, ion-exchange chromatography or the like, and any combinations of these methods can remove free fatty acids and refine the monoglycerides in high purities. The methods in combination with the distillation method are particularly effective for such purification, and particularly for example the reaction mixture can be loaded on molecular distillation to remove unreacted free fatty acids as a cut and then to give refined monoglyceride fractions by the distillation of the monoglycerides.

In connection with the above described refinement method, this invention also relates to the following method for deacidification and purification of glycerides:

a process for deacidification and purification of a glyceride product comprising or comprising as a major ingredient a monoglyceride, wherein alkali is added to the glyceride product comprising or comprising as a major ingredient a monoglyceride concomitantly containing a free fatty acid to neutralize thereby the free fatty acid present in the product to produce a saponification product, and a material having a molecular weight higher than the monoglyceride and compatibility with the saponification product is added to decrease the concentration of the saponification product, which is then subjected to molecular distillation to remove the saponification product as the residue of distillation.

The above described deacidification and purification method can be effectively applied to the case where only a small amount (usually 20 mg KOH/g or less of acid value) of free fatty acids is present in a product containing as the main ingredient the above described conjugated fatty acid containing monoglyceride (e.g., conjugated linoleic acid containing monoglyceride). In addition, in the deacidification and distillation described above, the deacidification and purification method can be applied to the case where a free fatty acid is concomitantly present in the residual fraction (comprising the conjugated fatty acid containing monoglyceride as a main component) in which the free fatty acid has been removed by distillation or the case where further refinement is desired because of the expectation of the still remaining contamination of a free fatty acid in the conjugated fatty acid monoglyceride fractions which are obtained as distillates by the distillation of the residual fraction as "the glyceride product comprising as the main ingredient the monoglyceride which concomitantly contains the free fatty acids". Preferred examples are illustrated below.

First, alkali (preferably sodium hydroxide, potassium hydroxide, calcium hydroxide, etc.) is added in an equimolar amount to free fatty acids still concomitantly present in the glyceride product which contains as the main ingredient the monoglyceride concomitantly containing the free fatty acids to decrease the acid value to 0–10 mg KOH/g, preferably 0–5 mg KOH/g, more preferably 0–3 mg KOH/g, thus producing the saponification product of the fatty acids. Then, a material having compatibility to the saponification product and a higher molecular weight or boiling point than the monoglyceride is added, and the mixture is subjected to molecular distillation at 180° C.–250° C. under a vacuum of 0.5–0.005 mmHg. Such materials preferably include for example diglycerides and triglycerides, and cholesterol esters, waxes, sugar esters and the like may be used as well. Molecular distillation can be conducted with conventional molecular distillation apparatuses. As a result of molecular distillation, the monoglyceride can be recovered as a distillate, and the saponification products, added materials compatible to the saponification products and higher boiling substances (comprising as main ingredients diglycerides and triglycerides) contaminated in the reaction mixture (monoglyceride fraction) can be removed as the distillation residues. In this connection, the amount of the materials compatible to the saponification products can be appropriately set, and the monoglyceride can be most efficiently distilled and refined when the amount of the materials is set at the lowest amount that the viscosity of the distillation residue can be decreased to a level where the distillation operation will not disturbed.

As the object of refinement, that is, the glyceride product comprising or comprising as the main ingredient a monoglyceride which contains concomitantly a free fatty acid, it is possible to use a product comprising as the main ingredient a conjugated fatty acid containing monoglyceride obtained by the method of this invention as above and a partially purified product thereof (a partial refinement product in which the free fatty acid has been partly removed from the reaction mixture by molecular distillation) as well as any glyceride products which comprise free fatty acid-concomitantly containing monoglycerides such as non-conjugated fatty acid containing glyceride products (which may contain di- or triglyceride) obtained by conventional chemical or enzymatic methods or partially purified products thereof. As non-conjugated fatty acid in the non-conjugated fatty acid containing glyceride products, non-conjugated fatty acids corresponding to the conjugated fatty acids mentioned above, for example linoleic acid can be exemplified.

In this invention, the esterification degree was expressed by the amount of fatty acids reacted (the amount of fatty acids consumed by the reaction) to the amount of free fatty acids before reaction, and the amount of the free fatty acids were determined from the acid value measured by alkalimetry. The composition of the glycerides was analyzed by developing the glycerides with benzene/chloroform/acetic acid (50:20:0.5) followed by quantification with a TLC/FID analyzer (IATROSCAN). The composition of the fatty acids in the monoglycerides was analyzed by methyl esterification of the constituent fatty acids followed by gas chromatography equipped with a DB-23 capillary column (0.25 mm×30 mm).

EXAMPLES

This invention is further specifically illustrated hereinafter with reference to examples, but it is not limited by these examples.

Example 1

Effect of the Amount of Glycerol:*Penicillium camembertii* Mono- and Di-Glyceride Lipase As the mixture of free fatty acids containing conjugated linoleic acid, the product of Rinoru Oil Mills. Co. CLA-80 (c9,t11-CLA, 33.1%; t10,c12-CLA, 33.9%; c9,c11-CLA, 0.9%; c10,c12-CLA, 1.4%; other CLA, 1.8%) was used. The reaction was carried out in a vial bottle having a 50 ml volume under stirring with a stirrer at 500 rpm. The reaction mixture consisting of 5 g of a CLA-80/glycerol (1:1–10, mole/mole) and 0.1 ml of an aqueous solution of *Penicillium camembertii* mono- and di-glyceride lipase (200 mg/ml, 10000 U/ml; Amano Enzyme; Lipase G) was incubated with stirring at 30° C. for 24 hours. The compositions of the reaction mixtures and the esterification degrees after reaction are shown in Table 1. When the esterification reaction was carried out at 30° C., the esterification degree reached 90% or more with 7 moles of glycerol per mole of the free fatty acids without dehydration under reduced pressure. In addition, no triglycerides were synthesized in the reaction, and the monoglycerides and the diglycerides in the glyceride fraction were synthesized approximately in equimolar amounts irrespective of the amounts of glycerol used as the substrate.

TABLE 1

| Fatty Acids/Glycerol (mole/mole) | Esterification degree (%) | Composition of Reaction Mixture (wt %) | | |
|---|---|---|---|---|
| | | Fatty Acids | Monoglycerides | Diglycerides |
| 1:1 | 64.0 | 36.0 | 30.2 | 33.8 |
| 1:2 | 78.8 | 21.2 | 38.8 | 40.0 |
| 1:5 | 83.4 | 16.6 | 40.7 | 42.7 |
| 1:7 | 91.1 | 8.9 | 43.0 | 48.1 |
| 1:10 | 91.9 | 8.1 | 43.6 | 48.2 |

Example 2

Effect of Temperature: *Penicillium camembertii* Mono- and Di-Glyceride Lipase

A reaction mixture consisting of 5 g of CLA-80/glycerol (1:5, mole/mole) and 0.1 ml of an aqueous solution of *Penicillium camembertii* mono- and di-glyceride lipase (10000 U/ml) was incubated under stirring with a stirrer (500 rpm) at a temperature in the range from 5° C.–50° C. The esterification degree and the compositions of the reaction mixture after 5 hours and 24 hours of the reaction are shown in Table 2. The esterification degree was increased along with the increase of the reaction temperature. When the reaction temperature was set at 30° C. or more, diglycerides were produced as by-products, but the conversion of the monoglycerides into the diglycerides were suppressed in the reaction at 15° C. or less.

TABLE 2

| Reaction Temperature (° C.) | Reaction Time (hours) | Esterification degree (%) | Composition of Reaction Mixture (wt %) | | |
|---|---|---|---|---|---|
| | | | Fatty Acids | Monoglycerides | Diglycerides |
| 5 | 5 | 49.5 | 50.5 | 49.1 | 0.4 |
| | 24 | 88.6 | 11.4 | 83.8 | 4.8 |
| 15 | 5 | 66.8 | 33.1 | 64.8 | 2.1 |
| | 24 | 87.9 | 12.1 | 80.5 | 7.4 |
| 30 | 5 | 81.1 | 18.9 | 55.4 | 25.7 |
| | 24 | 85.8 | 14.2 | 44.7 | 41.1 |
| 40 | 5 | 82.6 | 17.4 | 58.6 | 24.0 |
| | 24 | 86.1 | 13.9 | 46.9 | 39.2 |
| 50 | 5 | 82.1 | 17.9 | 55.5 | 26.4 |
| | 24 | 86.1 | 13.9 | 45.3 | 40.8 |

Example 3

Process for producing conjugated linoleic acid containing monoglycerides with esterification reaction alone in the presence of *Penicillium camembertii* mono- and di-glyceride lipase as a catalyst The reaction was carried out in a four-neck round bottom flask having a volume of 1000 ml, and stirring was carried out with a WALL WETTER (KANSAI KAGAKU KIKAI SEISAKU (K.K.)). The reaction was initiated with a mixture of 300 g of CLA-80/glycerol (1:3, mole/mole) and 6 ml of an aqueous solution of *Penicillium camembertii* mono- and di-glyceride lipase (10000 U/ml) with stirring (250 rpm) at 5° C. As the fluidity of the reaction mixture was decreased with the passage of reaction, the stirring rate was decreased to 100 rpm after 10 hours when the esterification degree reached 38.7%, and to 50 rpm after 12 hours when the esterification degree reached 48%. The esterification degree reached 88.2% after 24 hours of the reaction, the reaction mixture was completely solidified and no effect of stirring was observed, so that the stirring was stopped. Then, the reaction was continued with dehydration under reduced pressure at 3 mmHg for further 48 hours (total reaction time, 72 hours) while the reaction mixture was left standing in order to further increase the esterification degree. The esterification degree and the compositions of the reaction mixture with the passage of reaction are shown in Table 3. After the esterification rate reached the constant level, it was possible to increase the esterification degree to a level of 97.1% by dehydration under reduced pressure. In addition, when the reaction was carried out at a low temperature, almost no diglycerides as the by-products were observed, and the monoglyceride content of the glyceride fraction reached 97.0% when the reaction was completed.

TABLE 3

| Reaction Time (hours) | Esterification degree (%) | Composition of Reaction Mixture (wt %) | | |
|---|---|---|---|---|
| | | Fatty Acids | Monoglycerides | Diglycerides |
| 0 | 0 | 100 | 0 | 0 |
| 2 | 2.1 | 97.9 | 1.7 | 0.4 |
| 4 | 6.2 | 93.8 | 5.4 | 0.7 |
| 7 | 15.0 | 85.0 | 14.4 | 0.6 |
| 10 | 38.7 | 62.3 | 36.4 | 1.3 |
| 12 | 48.0 | 52.0 | 46.8 | 1.2 |
| 24 | 88.2 | 11.8 | 84.4 | 3.7 |
| 28 | 92.9 | 7.1 | 89.3 | 3.6 |
| 34 | 94.2 | 5.8 | 90.8 | 3.4 |
| 48 | 96.5 | 3.5 | 94.0 | 2.5 |
| 72 | 97.1 | 2.9 | 94.2 | 2.9 |

Example 4

Process for Producing Conjugated Linoleic Acid Containing Monoglycerides with Esterification Reaction Alone in the Presence of *Penicillium camembertii* Mono- and Di-Glyceride Lipase as a Catalyst The reaction was carried out in a four-neck round bottom flask having a volume of 1000 ml, and stirring was carried out with a WALL WETTER (KANSAI KAGAKU KIKAI SEISAKU (K.K.)). The reaction was initiated with a mixture of 300 g of CLA-80/glycerol (1:5, mole/mole) and 6 ml of an aqueous solution of *Penicillium camembertii* mono- and di-glyceride lipase (10000 U/ml) with stirring (280 rpm) at 30° C. At the same time of the initiation of reaction, dehydration was initiated under reduced pressure of 5 mmHg, and the reaction was continued for 48 hours. The esterification rate and the compositions of the reaction mixture with the passage of reaction are shown in Table 4. It was possible to increase the esterification degree to a level of 97.0%, with the reaction mixture being liquid state, by dehydration under reduced pressure from the initiation of the reaction. In addition, diglycerides were scarcely observed as the by-products, and the monoglyceride content reached 89.3% when the reaction was completed.

TABLE 4

| Reaction | Composition of Reaction Mixture (wt %) | | | |
|---|---|---|---|---|
| Time (hours) | Esterification degree (%) | Fatty Acids | Monoglycerides | Diglycerides |
| 0 | 0 | 100 | 0 | 0 |
| 2 | 44.2 | 55.8 | 42.4 | 1.8 |
| 4 | 73.5 | 26.6 | 71.0 | 2.4 |
| 7 | 85.1 | 14.9 | 81.3 | 3.8 |
| 9 | 87.5 | 12.5 | 81.6 | 5.9 |
| 24 | 94.8 | 5.2 | 89.8 | 5.0 |
| 28 | 95.6 | 4.4 | 89.0 | 6.6 |
| 34 | 97.2 | 2.8 | 90.0 | 7.2 |
| 48 | 97.0 | 2.9 | 89.3 | 7.8 |

Example 5

Process for Producing Conjugated Linoleic Acid Containing Monoglycerides with Esterification and Glycerolysis Reactions in the Presence of *Penicillium camembertii* Mono- and Di-Glyceride Lipase as a Catalyst The reaction was initiated with the same reaction composition using the same apparatus as described in Example 3 at 30° C. with stirring at 250 rpm. After 9 hours when the esterification rate reached 84.0%, the reaction was continued with dehydration under reduced pressure at 3 mmHg and with stirring until the time of 72 hours. The reaction mixture was taken out in a beaker, which was put in ice-water to completely solidify the reaction mixture with stirring by a cooking handy mixer, and left standing at 5° C. for one week. The esterification degree and the compositions of the reaction mixture with the passage of reaction are shown in Table 5. The esterification degree was increased to a level of 96.5%, after 72 hours, by dehydration under reduced pressure after it reached the constant level. The monoglycerides and the diglycerides were present approximately in equimolar amounts in the glyceride fraction of the reaction mixture. If the reaction mixture taken out was solidified and then left standing at 5° C., the diglycerides were converted to the monoglycerides by undergoing glycerolysis. After one week (total reaction period, 10 days), the monoglyceride content in the glyceride fraction increased to 95.0% although the esterification degree was not substantially changed.

TABLE 5

| Reaction | Composition of Reaction Mixture (wt %) | | | |
|---|---|---|---|---|
| Time (hours) | Esterification degree (%) | Fatty Acids | Monoglycerides | Diglycerides |
| 0 | 0 | 100 | 0 | 0 |
| 1 | 48.3 | 51.7 | 46.2 | 2.1 |
| 2 | 71.4 | 28.6 | 66.9 | 4.5 |
| 4 | 80.8 | 19.2 | 64.6 | 16.2 |
| 7 | 81.9 | 18.1 | 56.6 | 25.3 |
| 9 | 84.0 | 16.0 | 59.7 | 24.3 |
| 24 | 90.6 | 9.4 | 48.7 | 41.9 |
| 48 | 94.6 | 5.4 | 46.5 | 48.1 |
| 72 | 96.5 | 3.5 | 47.6 | 48.9 |
| 120 | 97.3 | 2.7 | 69.1 | 28.2 |
| 168 | 96.5 | 3.5 | 84.1 | 11.4 |
| 240 | 96.9 | 3.1 | 92.1 | 4.8 |

Example 6

Process for Producing Conjugated Linoleic Acid Monoglycerides with Esterification Reaction Alone in the Presence of *Candida rugosa* Lipase as a Catalyst The reaction was carried out using the same apparatus as in Example 3. The reaction was initiated with a mixture of 300 g of CLA-80/glycerol (1:5, mole/mole) and 7.5 ml of an aqueous solution of *Candida rugosa* lipase (100 mg/ml; 35000 U/ml; Meito Sangyo Co., Ltd.; Lipase OF) with stirring (250 rpm) at 5° C. As the fluidity of the reaction mixture was decreased with the passage of reaction, the stirring rate was decreased to 100 rpm after 4 hours when the esterification rate reached 37.7%, and to 50 rpm after 7 hours when the esterification degree reached 55.8%. The esterification degree reached 88.1% after 24 hours of the reaction, the reaction mixture was completely solidified and no effect of stirring was observed, so that the stirring was stopped. In the reaction, the esterification degree reached 95% or more without dehydration under reduced pressure, and thus dehydration was not conducted during reaction. The esterification degree and the compositions of the reaction mixture with the passage of reaction are shown in Table 6. Due to the esterification reaction at a low temperature, the diglycerides and the triglycerides as the by-products were scarcely observed. The monoglyceride content in the glyceride fraction increased to 95.4% when the reaction was completed.

TABLE 6

| Reaction | Composition of Reaction Mixture (wt %) | | | | |
|---|---|---|---|---|---|
| Time (hours) | Esterification degree (%) | Fatty Acids | Monoglycerides | Diglycerides | Triglycerides |
| 0 | 0 | 100 | 0 | 0 | 0 |
| 2 | 29.3 | 70.7 | 26.9 | 2.4 | 0 |
| 4 | 37.7 | 62.3 | 33.7 | 4.0 | 0 |
| 7 | 55.8 | 44.2 | 49.7 | 6.1 | 0 |
| 10 | 62.9 | 37.1 | 51.5 | 11.4 | 0 |
| 24 | 88.1 | 11.9 | 76.9 | 9.9 | 1.3 |
| 48 | 94.4 | 5.6 | 86.5 | 6.9 | 1.0 |
| 72 | 96.0 | 4.0 | 91.6 | 3.2 | 1.1 |

Example 7

Process for producing conjugated linoleic acid containing monoglycerides with esterification and glycerolysis reactions in the presence of *Alcaligenes* lipase as a catalyst The reaction was carried out using the same apparatus as in Example 3. The reaction was initiated with a mixture of 300 g of CLA-80/glycerol (1:3, mole/mole) and 33 ml of an aqueous solution of *Alcaligenes* sp. lipase (50 mg/ml; 1800 U/ml; Meito Sangyo Co., Ltd.; Lipase OF) with stirring (250 rpm) at 30° C. After 20 hours when the esterification rate reached 36.4%, the reaction was continued with dehydration under reduced pressure at 3 mmHg and with stirring until 30 hours. The reaction mixture was taken out in a beaker, which was put in ice-water and stirred with a handy mixer for cooking, but it was not solidified and left standing at 5° C. for one day. While the reaction mixture was solidified, it was warmed to afford fluidity, cooled on ice-water to completely solidify the reaction mixture with stirring with a mixer, and then left standing at 5° C. for 4 days. The esterification degree and the compositions of the reaction mixture with the passage of reaction are shown in Table 7. After the esterification degree reached the constant level, dehydration under reduced pressure increased the esterification degree to a level of 96.4% after 30 hours. The glyceride fraction in the reaction mixture contain mono-, di- and triglycerides. The reaction mixture taken out was left standing at 5° C. and solidified by stirring in the course of the reaction. Thus, the di- and triglycerides were converted to the monoglycerides by undergoing glycerolysis. The monoglyceride content of the glyceride fractions after 150 hours of the total reaction time increased to 90.3%, and the esterification degree was not changed by allowing to stand at a low temperature.

TABLE 7

| Reaction | Composition of Reaction Mixture (wt %) | | | |
|---|---|---|---|---|
| Time (hours) | Esterification degree (%) | Fatty Acids | Monoglycerides | Diglycerides | Triglycerides |
| 0 | 0 | 100 | 0 | 0 | 0 |
| 7 | 23.4 | 76.6 | 7.4 | 10.1 | 5.9 |
| 20 | 36.4 | 63.6 | 12.2 | 16.6 | 7.7 |
| 25 | 85.8 | 14.2 | 29.8 | 41.0 | 15.0 |
| 30 | 96.4 | 3.6 | 14.9 | 54.3 | 27.2 |
| 54 | 95.1 | 4.9 | 50.9 | 34.2 | 10.0 |
| 102 | 96.8 | 3.2 | 76.3 | 19.4 | 1.1 |
| 150 | 96.2 | 3.8 | 86.9 | 8.4 | 0.9 |

Example 8

Conjugated Linoleic Acid Content in Monoglycerides

After dissolving the reaction mixtures prepared in Examples 3–7 by warming, the oil layers were recovered by centrifugation at 7000×g. The fatty acids in the glyceride fractions were methylated by the conventional methods using Na-methylate as a catalyst, and the compositions were analyzed and determined quantitatively by gas chromatography. The results are shown in Table 8. The fatty acids in the glyceride fractions had the same compositions as those of CLA-80 used as the raw material. It was found from these results that the mono- and diglyceride lipase of *Penicillium camembertii*, *Candida rugosa* lipase, and *Alcaligenes* lipase equally recognize all fatty acid species contained in CLA-80. Thus, it was possible to prepare the monoglycerides having the same compositions as those of the fatty acids contained in the raw material by using the method illustrated herein.

TABLE 8

| | | | | Conjugated Linoleic Acid | | | | |
|---|---|---|---|---|---|---|---|---|
| Sample Nos. | 16:0 | 18:0 | 18:1 | c9, t11 | t10, c12 | c9, c11 | c10, c12 | Others |
| Raw Material (CLA-80) | 6.7 | 2.7 | 17.0 | 33.1 | 33.9 | 0.9 | 1.4 | 1.8 |
| Example 3 | 6.6 | 2.8 | 17.3 | 32.7 | 34.2 | 1.0 | 1.3 | 2.1 |
| Example 4 | 7.0 | 2.5 | 18.1 | 32.3 | 33.5 | 1.0 | 1.6 | 1.9 |
| Example 5 | 6.5 | 2.9 | 16.9 | 33.0 | 34.6 | 0.9 | 1.5 | 2.0 |
| Example 6 | 7.0 | 2.5 | 18.1 | 32.3 | 33.5 | 1.0 | 1.6 | 1.9 |
| Example 7 | 6.7 | 2.6 | 17.1 | 33.4 | 34.2 | 0.8 | 1.4 | 1.6 |

Example 9

Purification of Monoglycerides by Distillation Method

To 200 g of the reaction mixture (having an acid value of 6.01 mg KOH/g) obtained in Example 5 was added 4.28 ml of 5N KOH, followed by 200 g of safflower oil. After dehydration, the mixture was loaded on a molecular distillation apparatus (Sinko Pantec Co., Ltd.; Wiprene type 2-03) to refine the monoglycerides. First, after the low-boiling point materials (7.9 g) were removed at 120° C. under vacuum of 0.2 mmHg, distillation was further continued at 180° C. under vacuum of 0.2 mmHg to give 9.1 g of a distillate. The free fatty acids are conventionally distilled under this distillation condition. Nevertheless, the result that monoglycerides were not distilled revealed that free fatty acids and monoglycerides can be roughly fractionated by molecular distillation. Next, distillation was conducted at 200° C. under vacuum of 0.005 mmHg to give 181.3 g of a distillate. The distillate had an acid value of 1.8 mg KOH/g and a weight ratio of monoglyceride/diglyceride/free fatty acid of 97.2:1.9:0.9. Thus, it was recognized that free fatty acids concomitantly contained in a small amount in the mixture are effectively removed by the method of distillation fractionation after saponification.

Advantages Obtained by the Present Invention

As described above, this invention can provide conjugated fatty acid (typically conjugated linoleic acid) containing monoglycerides which contains a high ratio of monoglyceride.

According to the process of the invention, all kinds of lipases (including monoglyceride lipase, diglyceride lipase and triglyceride lipase) can be used as a catalyst, and conjugated fatty acid containing monoglycerides which contain a high ratio of monoglycerides as described above can be prepared.

In addition, by the use of lipase as a catalyst, it is possible to esterify 90% or more of the conjugated fatty acids and increase the conjugated fatty acid monoglyceride content in the glyceride fraction to a level of 80% or more by using the esterification reaction in which the conjugated fatty acids and glycerol are reacted at a low temperature, or by using the combination of the esterification reaction at a high temperature and the glycerolysis reaction at a low temperature in the same reaction system.

What is claimed is:

1. A process for producing a conjugated fatty acid containing monoglyceride comprising subjecting a conjugated fatty acid containing free fatty acid and glycerol to an esterification reaction in the presence of lipase as a catalyst, wherein glycerol is employed in an amount of 1–20 moles per mole of the free fatty acid containing a conjugated fatty acid to carry out the reaction at a temperature of 0° C.–20° C., and to maintain the temperature at 0° C.–20° C. until the esterification degree reaches a level of 90% or more.

2. A process according to claim 1, wherein a mixture of a substrate and an enzyme is formed into an emulsion by the stirring-like operation to carry out the reaction, the stirring-like operation is stopped when the fluidity of the emulsion is lowered and solidified, and the reaction is maintained at the predetermined temperature until the esterification degree reaches a level of 90% or more.

3. A process according to claim 1, wherein the esterification velocity and the esterification degree are enhanced by dehydration under reduced pressure in the course of the reaction.

4. A process for producing a conjugated fatty acid containing monoglyceride comprising subjecting a conjugated fatty acid containing free fatty acid and glycerol to esterification reaction in the presence of lipase as a catalyst, wherein glycerol is employed in an amount of 1–20 moles per mole of the free fatty acid containing a conjugated fatty acid to carry out the reaction at a temperature of 20° C.–50° C., to maintain the temperature at 20° C.–50° C., until the esterification rate reaches a level of 90% or more, and to dehydrate under reduced pressure from the start of the reaction for enhancing the esterification velocity and the esterification degree.

5. A process for producing a conjugated fatty acid containing monoglyceride comprising subjecting a conjugated fatty acid containing free fatty acid and glycerol to esterification and glycerolysis reactions in the presence of lipase as a catalyst, wherein glycerol is employed in an amount of 1–20 moles per mole of the free fatty acid containing the conjugated fatty acid to carry out the esterification reaction at a temperature of 20° C.–70° C., to dehydrate under reduced pressure in the course of the reaction for enhancing the esterification degree to a level of 90% or more and then cooling the reaction system, and to allow to stand the system at a temperature of 0° C.–20° C. for advancing the glycerolysis reaction.

6. A process according to claim 5, wherein a mixture of a substrate and an enzyme is formed into an emulsion by the stirring-like operation to carry out the esterification reaction, and after the esterification degree reaches the level of 90% or more the reaction fluid is rapidly cooled with the strong stirring-like operation until it is solidified.

7. A process according to claim 1, wherein the conjugated fatty acid is conjugated linoleic acid.

8. A process according to claim 4, wherein the conjugated fatty acid is conjugated linoleic acid.

9. A process according to claim 5, wherein the conjugated fatty acid is conjugated linoleic acid.

10. A process according to claim 1, wherein the monoglyceride contains a conjugated fatty acid in an amount of 50% or more in the total fatty acids.

11. A process according to claim 4, wherein the monoglyceride contains a conjugated fatty acid in an amount of 50% or more in the total fatty acids.

12. A process according to claim 5, wherein the monoglyceride contains a conjugated fatty acid in an amount of 50% or more in the total fatty acids.

13. A process according to claim 1, wherein the ratio of the monoglyceride in the total glycerides is 50% by weight or more.

14. A process according to claim 4, wherein the ratio of the monoglyceride in the total glycerides is 50% by weight or more.

15. A process according to claim 5, wherein the ratio of the monoglyceride in the total glycerides is 50% by weight or more.

16. A process according to claim 2, wherein the esterification velocity and the esterification degree are enhanced by dehydration under reduced pressure in the course of the reaction.

* * * * *